United States Patent
Yoo et al.

(10) Patent No.: US 7,581,283 B2
(45) Date of Patent: Sep. 1, 2009

(54) NOZZLE ASSEMBLY HAVING UV GENERATION UNIT AND VACUUM CLEANER HAVING THE SAME

(75) Inventors: Dong-hun Yoo, Gwangju (KR); Jang-keun Oh, Gwangju (KR)

(73) Assignee: Samsung Gwangju Electronics Co., Ltd., Gwangju (KR)

( * ) Notice: Subject to any disclaimer, the term of this patent is extended or adjusted under 35 U.S.C. 154(b) by 16 days.

(21) Appl. No.: 12/077,227

(22) Filed: Mar. 18, 2008

(65) Prior Publication Data
US 2009/0133214 A1    May 28, 2009

(30) Foreign Application Priority Data
Nov. 27, 2007    (KR) .................. 10-2007-0121719

(51) Int. Cl.
*A47L 9/28*    (2006.01)
(52) U.S. Cl. .................. 15/319; 15/324; 15/339; 15/246.3
(58) Field of Classification Search .................. 15/319, 15/324, 339, 246.3; *A47L 9/28*
See application file for complete search history.

(56) References Cited

U.S. PATENT DOCUMENTS

| | | |
|---|---|---|
| 4,907,316 A | 3/1990 | Kurz |
| 7,251,853 B2 * | 8/2007 | Park et al. .................. 15/319 |
| 2007/0143954 A1 | 6/2007 | Graham et al. .................. 15/364 |
| 2007/0192986 A1 | 8/2007 | Garcia et al. |
| 2007/0192987 A1 | 8/2007 | Garcia et al. |

FOREIGN PATENT DOCUMENTS

| | | |
|---|---|---|
| GB | 648967 | 7/1947 |
| KR | 1020060020562 | 3/2006 |

OTHER PUBLICATIONS

British Combined Search and Examination Report dated Dec. 16, 2008 corresponding to Application No. GB0815891.7.

* cited by examiner

*Primary Examiner*—David A Redding
(74) *Attorney, Agent, or Firm*—Ohlandt, Greeley, Ruggiero & Perle, L.L.P.

(57) ABSTRACT

A nozzle assembly having a UV generation unit and a vacuum cleaner having the same are provided. The nozzle assembly includes a nozzle main body that moves over a cleaning surface, a drum brush unit that is formed on the nozzle main body and includes an extension unit, an ultraviolet (UV) generation unit that is formed on the drum brush unit to be folded or unfolded so that the UV generation unit selectively faces the cleaning surface, and a switch that turns the UV generation unit on or off according to whether the UV generation unit is folded or unfolded.

12 Claims, 4 Drawing Sheets

_US 7,581,283 B2_

NOZZLE ASSEMBLY HAVING UV GENERATION UNIT AND VACUUM CLEANER HAVING THE SAME

CROSS-REFERENCE TO RELATED APPLICATIONS

This application claims the benefit under 35 U.S.C. § 119 (a) of Korean Patent Application No. 10-2007-0121719, filed in the Korean Intellectual Property Office on Nov. 27, 2007, the entire disclosure of which is incorporated herein by reference.

BACKGROUND OF THE INVENTION

1. Field of the Invention

The present disclosure relates to a vacuum cleaner. More particularly, the present disclosure relates to a nozzle assembly that sterilizes a cleaning surface by irradiating ultraviolet rays on the cleaning surface, and a vacuum cleaner having such a nozzle assembly.

2. Description of the Related Art

In general, a vacuum cleaner has a nozzle assembly for drawing in contaminants on a cleaning surface, that is, contaminants on a surface to be cleaned. Such a nozzle assembly draws in dust or contaminants in contact with the cleaning surface using suction force generated by a suction motor which is mounted inside a main body of a vacuum cleaner.

In particular, among the diverse nozzle assemblies, a nozzle assembly for an upright-type vacuum cleaner is rotatably connected to the underside of the main body of the vacuum cleaner, and includes a drum brush for brushing contaminants on a cleaning surface, such as carpet. However, such a conventional nozzle assembly cannot sterilize viruses or germs on a cleaning surface.

SUMMARY OF THE INVENTION

An aspect of embodiments of the present disclosure is to solve at least the above problems and/or disadvantages and to provide at least the advantages described below. Accordingly, an aspect of embodiments of the present disclosure is to provide a nozzle assembly which not only includes an ultraviolet (UV) generation unit for sterilizing a cleaning surface, but also selectively turns the UV generation unit on or off by simple manipulation.

In order to achieve the above-described and other aspects of embodiments of the present disclosure, a nozzle assembly is provided including a nozzle main body that moves over a cleaning surface, a drum brush unit that is formed on the nozzle main body and comprises an extension unit, an ultraviolet (UV) generation unit (formed on the drum brush unit to be folded or unfolded so that the UV generation unit selectively faces the cleaning surface), and a switching means that turns the UV generation unit on or off according to whether the UV generation unit is folded or unfolded.

The UV generation unit may generate UV rays if the UV generation unit is unfolded to face the cleaning surface, and the UV generation unit may not generate UV rays if the UV generation unit is folded.

The UV generation unit may include a housing that comprises a housing arm which is pivotably connected to the extension unit of the drum brush unit, a grill unit that is coupled to the housing and comprises a plurality of holes, and a UV lamp that is formed between the housing and the grill unit.

The switching means may include a microswitch that is turned on or off by selective interference of the housing arm.

The microswitch may be formed on the housing arm.

The microswitch may be formed on the extension unit.

The nozzle assembly may further include an elastic member that elastically supports the UV generation unit in a direction in which the UV generation unit is folded, and a locking unit that keeps the UV generation unit unfolded when the UV generation unit is unfolded.

The elastic member may include a spring that is formed at a pivot axis of the housing arm.

The locking unit may include a hook member that is formed at the drum brush unit to move vertically, and comprises a button at the upper part and a hook at the lower part, a spring that elastically supports the hook member upwards, and a locking part that is formed at the housing to be hooked by the hook of the hook member when the UV generation unit is unfolded to face the cleaning surface.

The locking part which is hooked by the hook of the hook member may be unlocked if the button of the hook member is pressed.

In order to achieve the above-described and other aspects of embodiments of the present disclosure, a nozzle assembly is provided including a nozzle main body that moves over a cleaning surface, a drum brush unit that is formed on the nozzle main body and comprises an extension unit, and an ultraviolet (UV) generation unit that is formed on the drum brush unit to be folded or unfolded so that the UV generation unit selectively faces the cleaning surface, wherein the UV generation unit generates UV rays if the UV generation unit is unfolded to face the cleaning surface, and the UV generation unit does not generate UV rays if the UV generation unit is folded.

In order to achieve the above-described and other aspects of embodiments of the present disclosure, a vacuum cleaner may be implemented by combination of the nozzle assembly and the main body described above.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 7 is a drawing illustrating a state in which the microswitch of FIG. 6 is pressed by an extension unit by rotating a housing arm so that the UV generation unit is turned on.

DETAILED DESCRIPTION OF THE EXEMPLARY EMBODIMENTS

Figure 1:
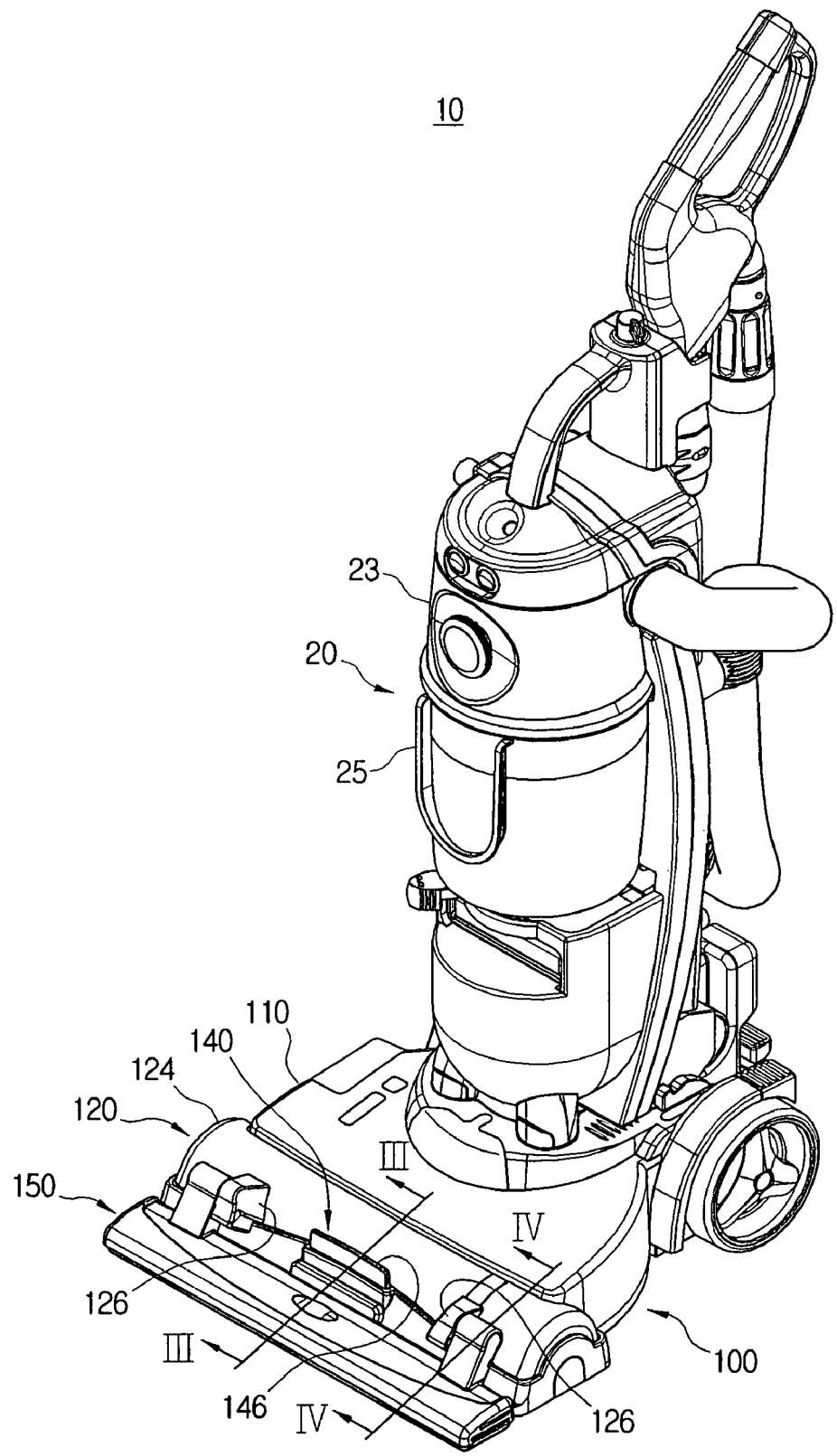
FIG. 1 is a perspective view illustrating an upright-type vacuum cleaner having a nozzle assembly in which a UV generation unit is mounted according to an exemplary embodiment of the present disclosure.

Reference will now be made in detail to the present embodiments of the present disclosure, examples of which are illustrated in the accompanying drawings, wherein like reference numerals refer to like elements throughout. The embodiments are described below in order to explain the present disclosure by referring to the figures.

Hereinafter, a nozzle assembly 100 including an ultraviolet (UV) generation unit according to an exemplary embodiment of the present disclosure is described with reference to FIGS. 1 to 5.

FIG. 1 is a perspective view illustrating an upright-type vacuum cleaner 10 having the nozzle assembly 100 in which the UV generation unit is mounted according to an exemplary embodiment of the present disclosure. As shown in FIG. 1, the nozzle assembly 100 having the UV generation unit is rotatably mounted on the underside of a vacuum cleaner main body 20 including a cyclone unit 23 and a dust receptacle 25. The nozzle assembly 100 includes a nozzle main body 110, a drum brush unit 120, a locking unit 140, and a UV generation unit 150.

The nozzle main body 110 may be formed integrally with or separately from the drum brush unit 120. An air path (not shown) is formed in the nozzle main body 110 to be connected to an air inlet 128 (see FIG. 3) which is formed in the drum brush unit 120. Accordingly, dust-laden air which is drawn in through the air inlet 128 passes through the air path of the nozzle main body 110 to the vacuum cleaner main body 20. In addition, a driving motor (not shown) for driving a drum brush 122 or a turbine (not shown) to be rotated by air drawn into the nozzle main body 110 may be formed in the nozzle main body 110. Since the configuration of the nozzle main body 110 is well-known in the related art, detailed description is not repeated here.

Figure 3:
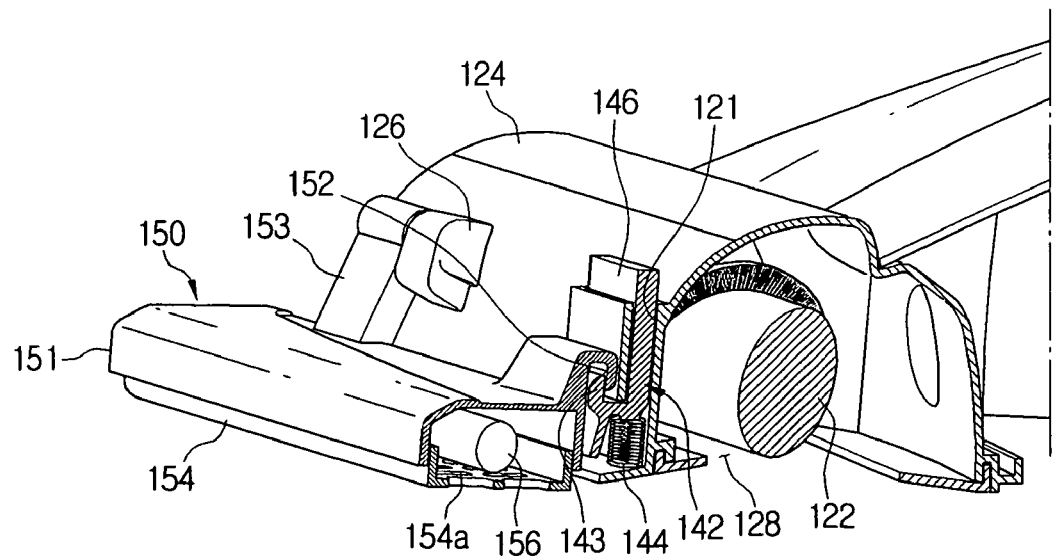
FIG. 3 is a cross-sectional view illustrating a nozzle assembly that is cut along line III-III of FIG. 1.

With reference to FIGS. 1 and 3, the drum brush unit 120 includes a drum brush 122, and a drum brush cover 124. The drum brush 122 rotates and strikes a cleaning surface, so contaminants can be separated from the cleaning surface. The drum brush 122 is rotatably formed inside the drum brush cover 124 to be surrounded by the drum brush cover 124. The drum brush 122 is connected to the turbine (not shown) or the driving motor (not shown) of the nozzle main body 110, and so can be rotated. Since the configuration of the drum brush 122 is also well-known in the related art, detailed description is not repeated here. Extension units 126 are formed integrally or by screw connection on both sides of the front of the drum brush cover 124, so the UV generation unit 150 can be rotatably connected to the front of the drum brush unit 120. A mounting space 121 is formed at the center of the front of the drum brush cover 124 to mount the locking unit 140. A microswitch 160 (see FIG. 5), which will be described in detail below, is formed inside the extension unit 126.

With reference to FIGS. 1 and 3, the locking unit 140 is mounted in the mounting space 121 at the front of the drum brush cover 124, and includes a hook member 142 and an elastic member 144. The hook member 142 moves vertically, and includes a button unit 146 on the upper part and a hook 143 on the lower part. The hook 143 is selectively locked with the locking part 152 of a housing 151 of the UV generation unit 150.

Figure 4:
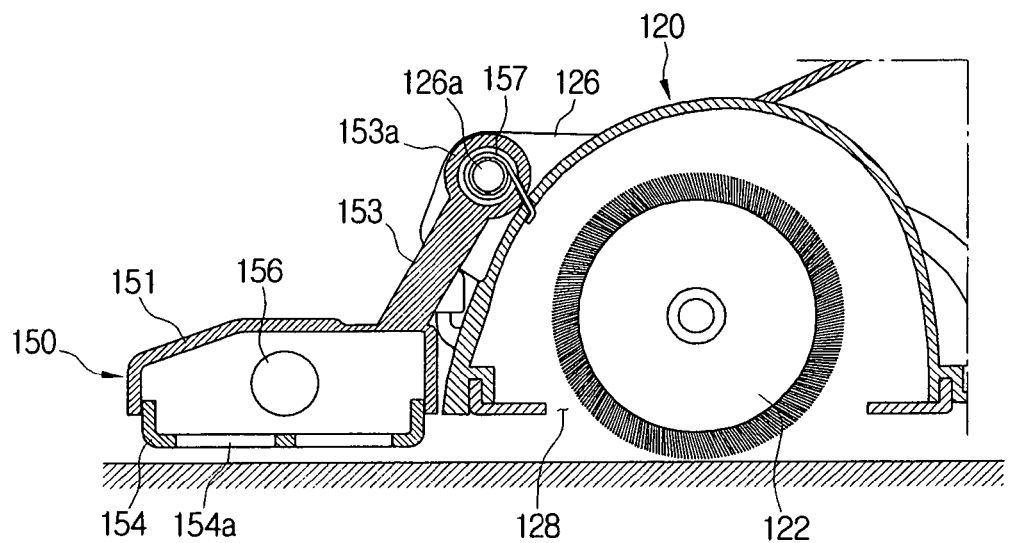
FIG. 4 is a cross-sectional view illustrating a nozzle assembly which is cut along line IV-IV of FIG. 1.
Figure 5:
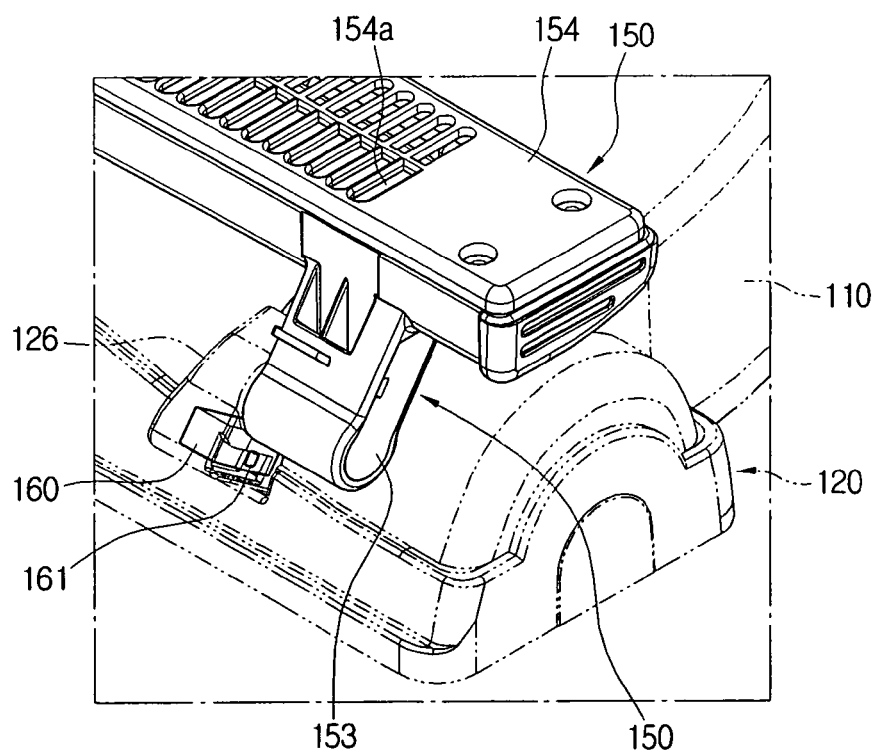
FIG. 5 is a drawing illustrating an installation state of a microswitch of a UV generation unit according to an exemplary embodiment of the present disclosure.

With reference to FIGS. 3 to 5, the UV generation unit 150 includes a housing 151, a grill unit 154, a UV lamp 156, and a microswitch 160.

With reference to FIG. 4, housing arms 153 protrude diagonally upwards from both sides of an upper surface of the housing 151. An end of the housing arm 153 is connected to a rotation axis 126a that extends from the extension unit 126 at the front of the drum brush cover 124. A spring 157 is formed on one end 153a of the housing arm 153 to elastically support the housing 151. That is, the spring 157 allows the housing 151 to be folded towards the upper part of the drum brush unit 120. The locking part 152 is formed at the center of the back of the housing 151 to be locked with the hook 143 of the hook member 142.

The grill unit 154 is coupled to the lower part of the housing 151, and the UV lamp 156 is mounted in a space defined by the coupling of the grill unit 154 and the housing 151. A plurality of grill holes 154a, formed on the grill unit 154, permit passage therethrough of ultraviolet rays generated by the UV lamp 156 to the cleaning surface.

With reference to FIG. 5, the microswitch 160 is used to turn the UV lamp 156 on or off, and is formed inside the extension unit 126. A button 161 is formed on one side of the microswitch 160, so the microswitch 160 can be turned on or off by pressing the button 161. The button 161 penetrates the extension unit 126 and protrudes from the extension unit 126. If the housing arm 153 presses the button 161 by rotation of the UV generation unit 150, the microswitch 160 is turned on, causing the UV lamp 156 to generate UV rays. If the housing arm 153 does not press the button 161, the microswitch 160 is turned off, causing the UV lamp 156 not to generate UV rays.

The operation of the nozzle assembly 100 having the UV generation unit 150 according to an exemplary embodiment of the present disclosure is described below.

Figure 2:
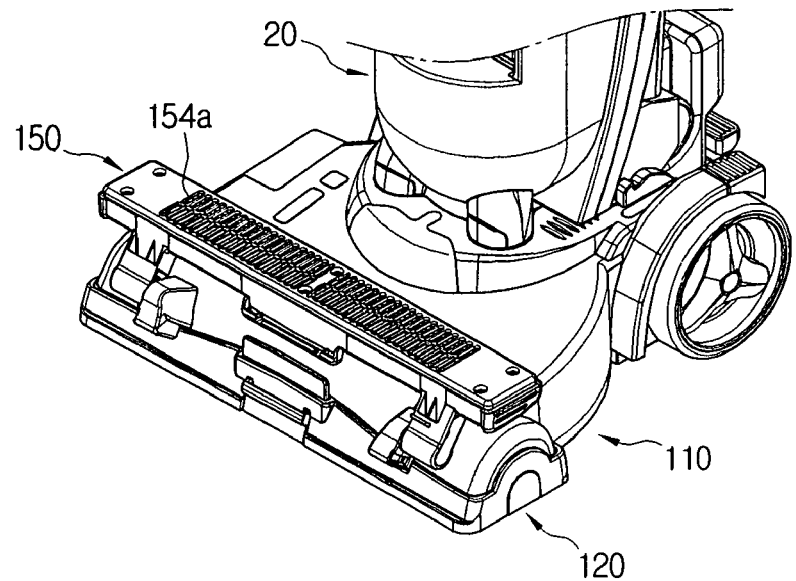
FIG. 2 is a drawing illustrating a folded state of the UV generation unit of FIG. 1.

With reference to FIGS. 1 to 5, in order for the user to sterilize a cleaning surface using the UV generation unit 150, when the UV generation unit 150 is folded on the upper part of the drum brush unit 120 as shown in FIG. 2, the user rotates the UV generation unit 150 using his/her hand or foot so that the grill unit 154 of the UV generation unit 150 faces the cleaning surface. In this case, since the spring 157 at one end 153a of the housing arm 153 is compressed in the opposite direction to the elastic force and the locking part 152 is locked with the hook 143, the UV generation unit 150 is fixed to the drum brush unit 120 by the locking unit 140. The housing arm 153 presses the button 161 of the microswitch 160 by being rotated downwards with respect to the extension unit 126. Accordingly, the microswitch 160 is turned on and so UV rays are radiated by the UV lamp 156 of the UV generation unit 150. As a result, the user can sterilize the cleaning surface by moving the nozzle assembly 100 back and forth and radiating UV rays onto the cleaning surface through the grill holes 154a of the grill unit 154.

If the user wishes to clean without using the UV generation unit 150, the user releases the connection between the locking part 152 and the hook 143 by pressing the button unit 146 on the hook member 142 downwards. Accordingly, the UV generation unit 150 is rotated upwards by elastic force of the springs 157 at one end 153a of the housing arms 153 and so is folded on the upper part of the drum brush cover 124. In addition, since the housing arms 153 are also rotated upwards with the UV generation unit 150, the pressed button 161 of the microswitch 160 is released and so the microswitch 160 is turned off. Consequently, the UV lamp 156 does not radiate UV rays.

In the nozzle assembly 100 having the UV generation unit according to an exemplary embodiment of the present disclosure, if the UV generation unit 150 is unfolded from the drum brush unit 120, UV rays are irradiated onto the cleaning surface. If the UV generation unit 150 is folded on the drum brush unit 120, UV rays are not generated. Accordingly, the user can turn the UV lamp 156 on or off by folding or unfolding the UV generation unit 150.

Figure 6:
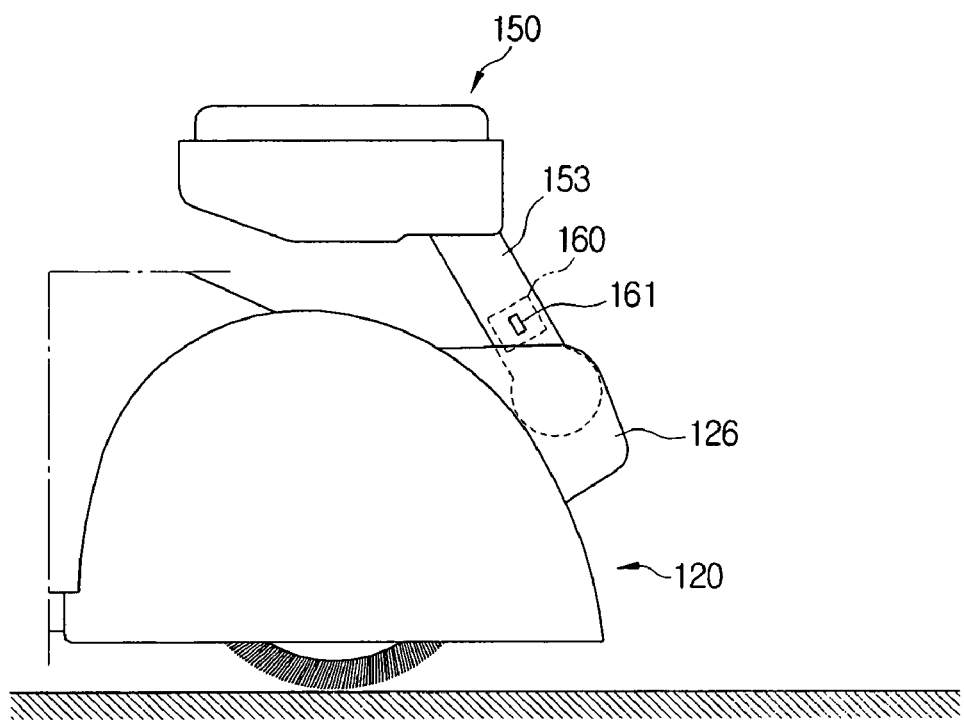
FIG. 6 is a drawing illustrating a state in which a microswitch of a UV generation unit is installed in a housing arm.
Figure 7:
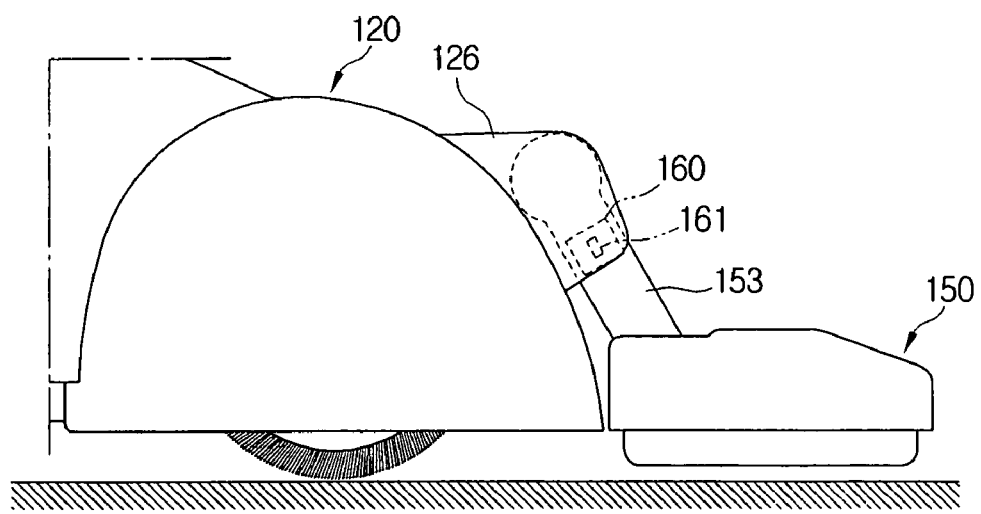

In the exemplary embodiment of the present disclosure, the microswitch 160 is formed inside the extension unit 126 and the button 161 of the microswitch 160 protrudes outside the extension unit 126. However, the micro switch 160 may be formed inside the housing arm 153 and the button 161 of the microswitch 160 may protrude outside the housing arm 153 as shown in FIG. 6. Accordingly, as shown in FIG. 7, the button 161 of the microswitch 160 can be pressed by the extension unit 126 upon rotating the housing arm 153.

As described above, the present disclosure enables the cleaning surface to be sterilized and can easily turn the UV lamp 156 on or off by simple operation of folding and unfolding the UV generation unit 150 with respect to the drum brush unit 120, causing the vacuum cleaner to be used easily.

While the invention has been shown and described with reference to certain embodiments thereof, it will be understood by those skilled in the art that various changes in form and details may be made therein without departing from the spirit and scope of the invention as defined by the appended claims.

What is claimed is:

1. A nozzle assembly, comprising:
    a nozzle main body that moves over a cleaning surface;
    a drum brush unit that is formed on the nozzle main body and comprises an extension unit;
    an ultraviolet (UV) generation unit that is formed on the drum brush unit to be folded or unfolded so that the UV generation unit selectively faces the cleaning surface; and
    a switch that turns the UV generation unit on or off according to whether the UV generation unit is folded or unfolded.

2. The nozzle assembly of claim 1, wherein the UV generation unit generates UV rays if the UV generation unit is unfolded to face the cleaning surface, and the UV generation unit does not generate UV rays if the UV generation unit is folded to not face the cleaning surface.

3. The nozzle assembly of claim 1, wherein the UV generation unit further comprises:
    a housing having a housing arm that is pivotably connected to the extension unit of the drum brush unit;
    a grill unit that is coupled to the housing and comprises a plurality of holes; and
    a UV lamp that is formed between the housing and the grill unit.

4. The nozzle assembly of claim 3, wherein the switch comprises a microswitch that is turned on or off by selective interference of the housing arm.

5. The nozzle assembly of claim 4, wherein the microswitch is formed on the housing arm.

6. The nozzle assembly of claim 4, wherein the microswitch is formed on the extension unit.

7. The nozzle assembly of claim 3, further comprising:
    an elastic member that elastically supports the UV generation unit in a direction in which the UV generation unit is folded; and
    a locking unit that keeps the UV generation unit unfolded when the UV generation unit is unfolded.

8. The nozzle assembly of claim 7, wherein the elastic member comprises a spring that is formed at a pivot axis of the housing arm.

9. The nozzle assembly of claim 7, wherein the locking unit comprises:
    a hook member that is formed at the drum brush unit to move vertically, and comprises a button at an upper part and a hook at a lower part;
    a spring which elastically supports the hook member upwards; and
    a locking part which is formed at the housing to be hooked by the hook of the hook member when the UV generation unit is unfolded to face the cleaning surface.

10. The nozzle assembly of claim 9, wherein the locking part that is hooked by the hook of the hook member is unlocked if the button of the hook member is pressed.

11. A nozzle assembly, comprising:
    a nozzle main body that moves over a cleaning surface;
    a drum brush unit that is formed on the nozzle main body and comprises an extension unit; and
    an ultraviolet (UV) generation unit that is formed on the drum brush unit to be folded or unfolded so that the UV generation unit selectively faces the cleaning surface,
    wherein the UV generation unit generates UV rays if the UV generation unit is unfolded to face the cleaning surface, and
    the UV generation unit does not generate UV rays if the UV generation unit is folded to not face the cleaning surface.

12. A vacuum cleaner, comprising:
    a main body that comprises a dust collecting unit; and
    a nozzle assembly, comprising
        a nozzle main body that moves over a cleaning surface;
        a drum brush unit that is formed on the nozzle main body and comprises an extension unit; and
        an ultraviolet (UV) generation unit that is formed on the drum brush unit to be folded or unfolded so that the UV generation unit selectively faces the cleaning surface,
        wherein the UV generation unit generates UV rays if the UV generation unit is unfolded to face the cleaning surface and the UV generation unit does not generate UV rays if the UV generation unit is folded to not face the cleaning surface,
    the nozzle assembly further being connected to the main body and moving on a cleaning surface.

* * * * *